United States Patent [19]
Cleveland

[11] 3,954,878
[45] May 4, 1976

[54] SYNTHESIS OF BIS(2-SUBSTITUTED ETHYLTHIOMETHYL) ETHERS

[75] Inventor: James P. Cleveland, Kingsport, Tenn.

[73] Assignee: Eastman Kodak Company, Rochester, N.Y.

[22] Filed: Oct. 23, 1974

[21] Appl. No.: 517,133

[52] U.S. Cl.............................. 260/609 R; 260/465 F
[51] Int. Cl.² ........................................ C07C 149/14
[58] Field of Search ...................... 260/609 R, 621 R

[56] References Cited
UNITED STATES PATENTS

| | | | |
|---|---|---|---|
| 2,442,339 | 6/1948 | Brittan et al. | 260/609 R |
| 2,551,421 | 5/1951 | Copenhaver | 260/609 R |
| 2,588,771 | 3/1952 | Schwartz | 260/609 R |
| 2,749,995 | 6/1956 | Klemm et al. | 260/609 R |
| 2,874,192 | 2/1959 | Cottle et al. | 260/609 R |

FOREIGN PATENTS OR APPLICATIONS

| | | | |
|---|---|---|---|
| 1,027,203 | 4/1958 | Germany | 260/609 R |

OTHER PUBLICATIONS

Reactions With Thioethoxide Ion in Dimethylformamide, Aust. J. Chem. 1972, 25, 1731–1735 and 1719–1729.

J. Am. Chem. Soc. Vol. 84 pp. 3777–3778 (1962).
Theilheimer Org. Reaction Vol. 2 p. 541.

*Primary Examiner*—Lewis Gotts
*Assistant Examiner*—D. R. Phillips
*Attorney, Agent, or Firm*—Elliott Stern; Daniel B. Reece, III

[57] ABSTRACT

Process for preparing bis(2-substituted ethylthiomethyl) ethers which comprises the steps of (1) reacting 2-hydroxyethyl mercaptan, or a 2-loweralkoxyethyl mercaptan with a bis(aryloxymethyl) ether having the formula $(ArOCH_2)_2O$ wherein Ar is a negatively substituted phenyl group, said reaction being carried out in the presence of an organic solvent and a strong base at a temperature of at least 60° to about 150°C. in an inert atmosphere and (2) extracting said bis(2-substituted ethylthiomethyl) ether. These compounds are useful intermediates in the preparation of bis(vinylsulfonylmethyl) ethers which are effective hardening agents for hardenable materials.

7 Claims, No Drawings

SYNTHESIS OF BIS(2-SUBSTITUTED ETHYLTHIOMETHYL) ETHERS

Bis(chloromethyl)ether is a very reactive and moderately volatile toxic, carcinogenic alkylating agent which is used to prepare α, α'-disubstituted dimethyl ether derivatives. These are used in the preparation of bis(-vinylsulfonylmethyl) ether, an effective hardening agent for hardenable materials in photographic elements. This invention describes a method for arriving at some sulfur-containing α, α'-disubstituted dimethyl ether derivatives without the use of bis(chloromethyl) ether. More specifically, this invention is directed to a process which allows the replacement of bis(-chloromethyl) ether with a bis(aryloxymethyl) ether which is much less reactive, nonvolatile and hence, less hazardous to use than bis(chloromethyl) ether.

Accordingly, there is provided a process for preparing bis-(2-substitutedethylthiomethyl) ethers which comprises the steps of 1) reacting two mole proportions of 2-hydroxyethyl mercaptan (mercaptoethanol) or a 2-lower-alkoxymethyl mercaptan with one mole proportion of a bis(aryloxymethyl) ether having the formula

(ArOCH$_2$)$_2$O wherein Ar is a negatively substituted phenyl group, the reaction being carried out in the presence of an organic solvent and a strong base at a temperature of at least 60° to about 150°C. in an inert atmosphere and (2) extracting the bis(2-substitutedethylthiomethyl) ether. The preferred mercaptan used according to this invention is 2-hydroxyethyl mercaptan.

Examples of suitable negatively substituted bis-(aryloxymethyl) ethers useful in this invention are those in which Ar is p-chlorophenyl, 2,4,6-dichlorophenyl, p-cyanophenyl, sulfonated phenyls, and the like. These compounds are known in the art and can be prepared by known methods. Preferably, chlorinated phenyls are most advantageously utilized.

Solvents useful in the process of this invention include, but are not limited to, dimethyl formamide, dimethyl sulfoxide, dimethyl acetamide, N-methylpyrrolidone, alcohols (such as butyl alcohol), and the cellosolves. It has been determined that reactions do, however, go faster in the aprotic rather than the protic solvents.

Bases which may be used in the process of this invention include sodium metal, sodium hydride, sodium methoxide, sodium hydroxide, potassium hydroxide, etc.

Since the reaction follows the following equation

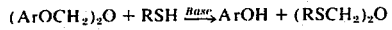
(ArOCH$_2$)$_2$O + RSH $\xrightarrow{Base}$ ArOH + (RSCH$_2$)$_2$O wherein R is 2-hydroxyethyl or 2-lower alkoxyethyl, e.g, methoxyethyl, ethoxyethyl, propoxyethyl, butoxyethyl, hexoxyethyl, two molar proportions of mercaptan are required to react with one mole of the bis-(aryloxy methyl) ether described above.

The reactions proceed readily by heating the reaction mixtures, at a temperature of at least 60° to about 150°C., preferably under an inert atmosphere, for a convenient length of time. Product recovery is accomplished readily by extraction with an organic solvent from the reaction mixture which has been drowned in water. Generally the coproduct, the appropriate negatively substituted phenol, is easily removed by extraction from the aqueous solution after removal of the bis(2-substituted-thiomethyl) ether. In the case of a water soluble product, such as bis2-hydroxyethylthiomethyl) ether, the phenol may be removed before or after removal of the sulfur-containing product. Yields are usually found to be equal to or greater than 75 percent and frequently are about 90 percent or above. Further purification of the bis(2-substitutedethyl thiomethyl) ether is usually unnecessary.

The compounds derived from the compounds prepared by the process of this invention can be used effectively in combination with hardenable materials in general, but they are most advantageously used with natural or synthetic polymers used as vehicles or binders in preparing photographic elements in the manner disclosed in U.S. Pat. No. 3,539,644, hereby incorporated by reference.

This invention can be further illustrated by the following examples of preferred embodiments thereof, although it will be understood that these examples are included merely for purposes of illustration and are not intended to limit the scope of the invention.

EXAMPLE 1 bis2-hydroxyethylthiomethyl) ether

To 500 ml. ethoxyethanol are added 174.5 g. (0.4 mole) bis-(trichlorophenoxymethyl) ether, 67.5 g. of 50% aqueous NaOH (0.84 mole NaOH), and 65.5 g. (0.84 mole) mercaptoethanol. The mixture is heated to reflux with stirring, and the solvent is slowly distilled off. After about 50 minutes, 390 ml. liquid has been removed, and the reaction is complete. About 500 ml. water is added and most of the residual ethoxyethanol solvent is azeotroped out after the distillation of 400 ml. liquid. About 500 ml. more water is added, and 150 ml. more distillate is removed. This gives an aqueous solution which contains no ethoxyethanol.

After the murky solution was cooled and filtered, 66 g. (1.1 mole acetic acid was added. The trichlorophenol was removed by extraction with 1000 ml. hot heptane followed by 300 ml. cold heptane. The aqueous solution was then made alkaline with 32 g. of 50% aqueous NaOH and salted with 125 g. NaCl. Extraction with dichloroethane (3 times, each with 200 ml.) followed by solvent removal gave 75.0 g. (>90%) bis(2-hydroxyethylthiomethyl) ether as a medium red oil. This oil was identified by infrared spectroscopy and gas-liquid chromatography and found to be identical to the material made from bis(chloromethyl) ether and mercaptoethanol described in Example II of U.S. Pat. No. 3,539,644.

EXAMPLE 2

Bis(2-vinylsulfonylmethyl) ether

The bissulfide prepared in Example 1 is oxidized to the disulfone by hydrogen peroxide according to the method of H. S. Schultz, et al, *J. Org. Chem.*, 28, 1140 (1963). The resulting diol is converted to 2,2'-bis(2-chloromethylsulfonyl) ether by adding two molar proportions of thionyl chloride to a refluxing solution of the diol and acetonitrile containing a catalytic amount of N,N-dimethylformamide. When the reacton is complete removal of the solvent and recrystallization from ethanol-acetone gives a high yield of a colorless chloride having a melting point of 83° to 84°C.

Dehydrohalogenation is effective in tetrahydrofuran solution at about 0° to 5°C. with two molar proportions of triethylamine. After 24 hours, the solvent is removed and the product recrystallized from a methanolethanol mixture giving colorless crystals having a melting point of 41.5° to 42.5°C.

The invention has been described in considerable detail with particular reference to certain preferred embodiments thereof, but it will be understood that variations and modifications can be effected within the spirit and scope of the invention as described above and as defined in the appended claims.

I claim:

1. Process for preparing bis (2-hydroxy or 2-alkoxy substituted ethylthiomethyl) ethers which comprises the steps of (1) reacting two mole proportions of 2-hydroxyethyl mercaptan or a 2-lower alkoxyethyl mercaptan with one mole proportion of a bis(aryloxymethyl) ether having the formula (ArOCH$_2$)$_2$O wherein Ar is a negatively substituted phenyl group, said reaction being carried out in the presence of an organic solvent selected from dimethyl formamide, dimetyl sulfoxide, dimethyl acetamide, N-methylpyrrolidone, butyl alcohol and ethoxyethanol and a strong aqueous base selected from sodium hydroxide and potassium hydroxide at a temperature of at least 60° to about 150°C. in an inert atmosphere and (2) extracting said bis(2-hydroxy or 2-lower alkoxy substituted ethylthiomethyl) ether.

2. The process of claim 1 wherein Ar is 2,4,6-trichlorophenyl.

3. The process of claim 2 wherein the solvent is butyl alcohol or ethoxyethanol and the base is sodium hydroxide.

4. The process of claim 3 wherein the mercaptan is 2-hydroxyethyl mercaptan.

5. The process of claim 1 wherein Ar is p-chlorophenyl.

6. The process of claim 5 wherein the solvent is ethoxyethanol or dimethylacetamide and the base is sodium hydroxide.

7. The process of claim 6 wherein the mercaptan is 2-hydroxyethyl mercaptan.

* * * * *